(12) United States Patent
Chen et al.

(10) Patent No.: US 12,141,234 B2
(45) Date of Patent: Nov. 12, 2024

(54) SYSTEMS AND METHODS FOR MRI DATA PROCESSING (71) Applicant: Shanghai United Imaging Intelligence Co., Ltd., Shanghai (CN)

(72) Inventors: Xiao Chen, Cambridge, MA (US);
Yikang Liu, Cambridge, MA (US);
Zhang Chen, Brookline, MA (US);
Shanhui Sun, Lexington, MA (US);
Terrence Chen, Lexington, MA (US);
Daniel Hyungseok Pak, New Haven, CT (US)

(73) Assignee: Shanghai United Imaging Intelligence Co., Ltd., Shanghai (CN)

( * ) Notice: Subject to any disclaimer, the term of this patent is extended or adjusted under 35 U.S.C. 154(b) by 366 days.

(21) Appl. No.: 17/741,323

(22) Filed: May 10, 2022

(65) Prior Publication Data
US 2023/0367850 A1    Nov. 16, 2023

(51) Int. Cl.
*G06F 18/214*  (2023.01)
*A61B 5/00*  (2006.01)
*G01R 33/56*  (2006.01)
*G06N 20/00*  (2019.01)
*G06T 11/00*  (2006.01)

(52) U.S. Cl.
CPC .......... *G06F 18/214* (2023.01); *A61B 5/7267* (2013.01); *G01R 33/5608* (2013.01); *G06N 20/00* (2019.01); *G06T 11/005* (2013.01)

(58) Field of Classification Search
CPC . G06F 18/214; A61B 5/7267; G01R 33/5608; G01R 33/4818; G06N 20/00; G06N 3/088; G06N 3/044; G06N 3/0464; G06N 3/084; G06T 11/005; G06V 2201/03; G06V 10/774
USPC ....................................................... 382/128
See application file for complete search history.

(56) References Cited

U.S. PATENT DOCUMENTS

| | | | |
|---|---|---|---|
| 11,185,249 B2 * | 11/2021 | Schlemper | ............... G06T 5/60 |
| 2008/0037851 A1 | 2/2008 | Takayama | |
| 2019/0369190 A1 * | 12/2019 | Ye | ........... G06N 3/045 |
| 2020/0342359 A1 * | 10/2020 | Hu | ........... G16H 30/40 |
| 2021/0192808 A1 | 6/2021 | Chen et al. | |
| 2022/0292679 A1 * | 9/2022 | Ahn | ........ G01R 33/565 |

(Continued)

*Primary Examiner* — Juan A Torres
(74) *Attorney, Agent, or Firm* — Zhong Law, LLC (57) ABSTRACT

Described herein are systems, methods, and instrumentalities associated with processing complex-valued MRI data using a machine learning (ML) model. The ML model may be learned based on synthetically generated MRI training data and by applying one or more meta-learning techniques. The MRI training data may be generated by adding phase information to real-valued MRI data and/or by converting single-coil MRI data into multi-coil MRI data based on coil sensitivity maps. The meta-learning process may include using portions of the training data to conduct a first round of learning to determine updated model parameters and using remaining portions of the training data to test the updated model parameters. Losses associated with the testing may then be determined and used to refine the model parameters. The ML model learned using these techniques may be adopted for a variety of tasks including, for example, MRI image reconstruction and/or de-noising.

20 Claims, 5 Drawing Sheets

(56) References Cited

U.S. PATENT DOCUMENTS

| | | | |
|---|---|---|---|
| 2023/0135995 A1* | 5/2023 | Chen | G06T 7/0012 |
| | | | 382/131 |
| 2023/0267719 A1* | 8/2023 | Parchami | G06V 10/82 |
| | | | 382/156 |
| 2023/0281809 A1* | 9/2023 | Song | G06N 3/084 |
| | | | 382/131 |

* cited by examiner

SYSTEMS AND METHODS FOR MRI DATA PROCESSING

BACKGROUND

Magnetic resonance imaging (MRI) has become an important tool for disease detection, noninvasive diagnosis, and treatment monitoring. MRI works by collecting signals from a spatial frequency domain, often referred as a k-space, and generating images based on the collected signals. The k-space and/or the images generated therefrom include complex-valued data, so ideally, to train an artificial neural network (ANN) to perform a MRI data processing task such as MRI image reconstruction, complex-valued data should be used for the training. In reality, however, medical MRI images that are available for conducting the training are usually stored in real-valued formats, such as Digital Imaging and Communications in Medicine (DICOM) formats, in which only the magnitudes of complex-valued MRI data (e.g., MRI images) are retained and the phase information of the complex-valued data is discarded. As a result, currently available training data cannot reflect the real world in ways that are relevant to practical use cases and artificial intelligence (AI) models trained using such data often lack accuracy and adaptability. Accordingly, systems, methods, and instrumentalities with improved AI models are highly desirable for MRI data processing.

SUMMARY

Described herein are systems, methods, and instrumentalities associated with processing MRI data (e.g., reconstructing an MRI image based on under-sampled MRI data) using a machine learning (ML) model. The ML model may be implemented using an artificial neural network (ANN) and the ML model may be learned using an instance of the ANN through a training process that comprises determining and storing initial parameters of the ML model and processing, based on the initial parameters of the ML model, a portion of a first MRI training dataset and a portion of a second MRI training dataset. A first set of updated parameters of the ML model and a second set of updated parameters of the ML model may be determined based on the processing of the first MRI training dataset and the processing of the second MRI training dataset, respectively, and the training process may further comprise processing, based on the first set of updated parameters of the ML model determined above, a remaining portion of the first MRI training dataset to determine a first loss, processing, based on the second set of updated parameters of the ML model determined above, a remaining portion of the second MRI training dataset to determine a second loss, and updating the initial parameters of the ML model based on the first loss and the second loss (e.g., based on a sum or an average of the first loss and the second loss).

In examples, the training process may further include processing, based on the initial parameters of the ML model, a portion of a third MRI training dataset to determine a third set of updated parameters of the ML model, processing, based on the third set of updated parameters of the ML model, a remaining portion of the third MRI training dataset to determine a third loss, and updating the initial parameters of the ML model further based on the third loss (e.g., based on a sum or an average of the first loss, second loss, and third loss described herein).

In examples, at least one of the first MRI training dataset or the second MRI training dataset may comprise complex-valued MRI data. The complex-valued MRI data may be actual MRI data (e.g., collected from clinical procedures) or they may be synthetically generated, for example, based on real-valued MRI data and by adding phase values to the real-valued MRI data. The phase values may be derived from an MRI image or as a function of one or more spatial locations associated with the real-valued MRI data.

In examples, at least one of the first MRI training dataset or the second MRI training dataset may comprise multi-coil MRI data that may be generated based on single-coil MRI data. For instance, the multi-coil MRI data may be generated by applying one or more coil sensitivity maps to the single-coil MRI data, wherein the one or more coil sensitivity maps may be derived based on a spatial distribution function or a multi-coil MRI image.

BRIEF DESCRIPTION OF THE DRAWINGS

A more detailed understanding of the examples disclosed herein may be had from the following description, given by way of example in conjunction with the accompanying drawing.

DETAILED DESCRIPTION

The present disclosure is illustrated by way of example, and not by way of limitation, in the figures of the accompanying drawings.

Figure 1:
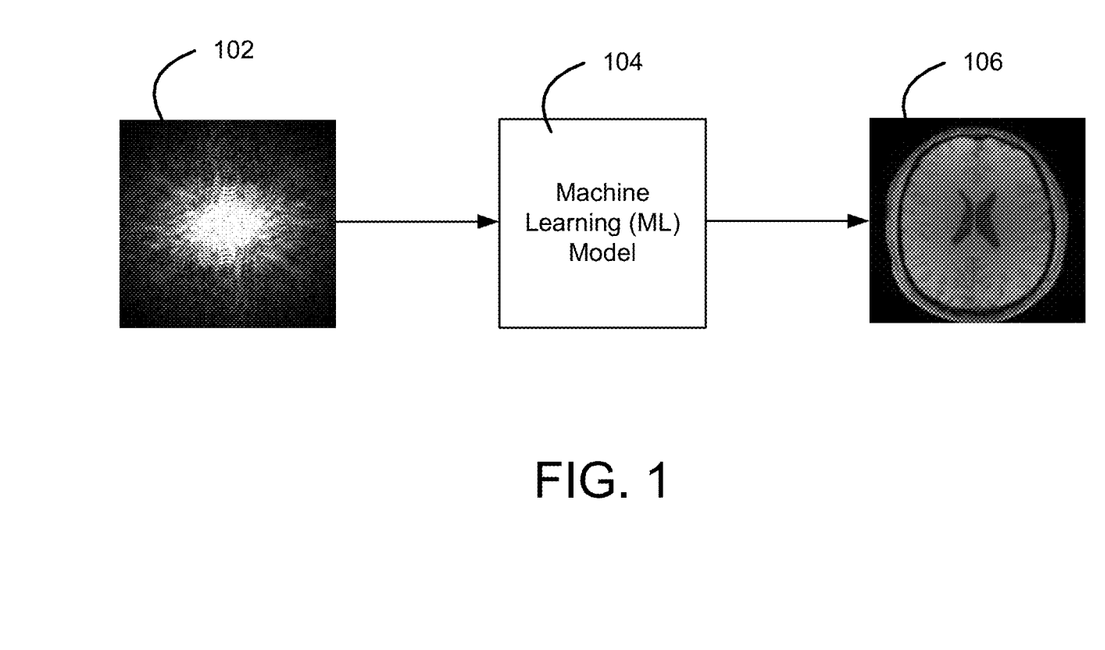
FIG. 1 is a simplified block diagram illustrating an example of processing MRI data using an ML model in accordance with one or more embodiments describe herein.

FIG. 1 illustrates an example of processing MRI data using deep learning based techniques such as a machine learning (ML) model. As shown, MRI data 102 associated with an anatomical structure such as the human brain may be collected from a spatial frequency domain referred to herein as a k-space (or k-space data/information). The MRI data may be inherently complex-valued (e.g., as they are measurements of rotating magnetization within a human body) and, as such, may include real and imaginary components. An ML model 104 may be trained to process MRI data 102 and produce a result such as an MRI image 106 that may be used for disease detection, noninvasive diagnosis, and/or treatment monitoring. The ML model may be implemented using an artificial neural network (ANN) such as a convolutional neural network (CNN), and the ML model (e.g., parameters of the ML model) may be learned, through a training process, based on real data or synthetically generated (e.g., computer-simulated based on real data) data. The ML model may be trained to perform different tasks including, for example, MRI image reconstruction, denoising, contrast enhancement, etc., and the data simulation and model training techniques described herein may be applied to any of these models and/or tasks.

Figure 2:
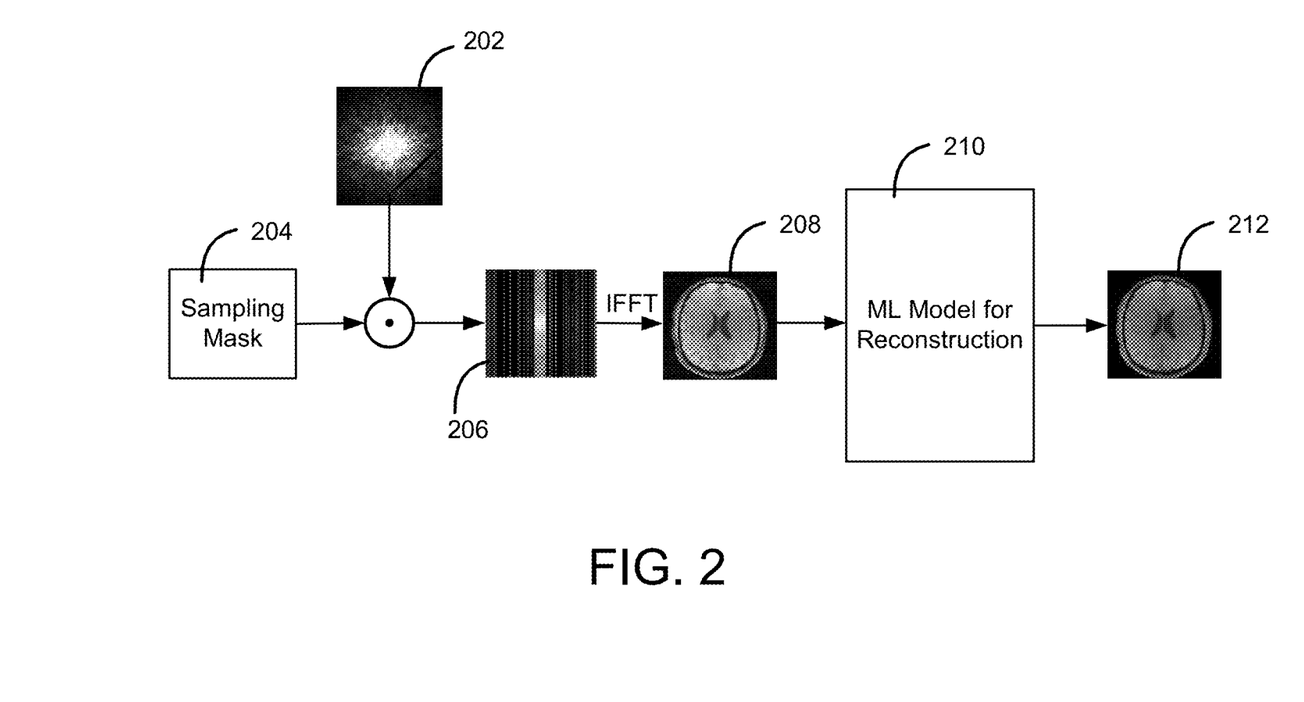
FIG. 2 is a simplified block diagram illustrating an example using a pre-trained ML model to reconstruct an MRI image based on the under-sampled data.

FIG. 2 illustrates an example of using a pre-trained ML model for MRI image reconstruction. As shown, when collecting data from k-space 202 for these tasks, a sampling mask (e.g., 204 shown in the figure) may be used to under-sample the k-space in order to accelerate the data collection and image generation process. For example, sampling mask 204 may include values corresponding to a plurality of locations of the k-space and the values may indicate whether data may be collected from each of those locations (e.g., a value "1" may indicate data collection at a location while a value of "0" may indicate no data collection at the location). The under-sampling operation may result in under-sampled MRI data 206 being collected, and the under-sampled data may be converted into an MRI image (e.g., 208 shown in the figure) via an inverse fast Fourier transform (IFFT). Since MRI data and MRI images may be converted back and forth using IFFT (e.g., from data to images) or FFT (e.g., from images to data), the term "MRI data" may be used interchangeably herein with the term "MRI images."

Since MRI image 208 may be generated from under-sampled MRI data 206, the image may lack details (e.g., compared to a fully-sampled MRI image) and/or may contain artifacts (e.g., aliasing artifacts) caused by the under-sampling. To recover the missing details and/or to remove the artifacts, ML model 210 may be used to reconstruct an MRI image (e.g., 212 shown in the figure) based on under-sampled image 208. Compared to under-sampled image 208, reconstructed MRI image 212 may be characterized by improved quality (e.g., having the same or substantially similar quality as if the image is generated based on fully sampled k-space data) and may be used to facilitate one or more downstream tasks such as T1 mapping. T2 mapping, etc.

The ML model described herein (e.g., ML model 104 of FIG. 1 and/or ML model 210 of FIG. 2) may be implemented and/or learned using an artificial neural network (ANN). For example, the ML model may be learned (e.g., during training) using a first instance of the ANN and may be implemented (e.g., at an inference time or a run time) using a second instance of the ANN. The ANN may have different structures dependent on the task that the ANN is trained to perform. For example, to perform image reconstruction and/or denoising, the ANN may include a convolutional neural network (CNN), and if the reconstruction and/or denoising involves multiple contrasts, the ANN may include a recurrent neural network (RNN) comprising one or more RNN blocks or cells (e.g., sub-networks), each of which may be configured to handle a corresponding one of the multiple contrasts.

A CNN used to perform the tasks or functions described herein may include a plurality of convolutional and/or transposed convolutional layers. Each of the convolutional layers may in turn include a plurality of convolution kernels or filters with respective weights (e.g., corresponding to parameters of the ML model implemented by the neural network) that may be configured to extract features from an input image (or data). The convolution operations may be followed by batch normalization and/or an activation function (e.g., such as a rectified linear unit (ReLu) activation function), and the features extracted by each of the convolutional layers may be down-sampled through one or more pooling layers and/or one or more fully connected layers to obtain a representation of the features, for example, in the form of a feature map or feature vector. In examples, the features extracted by the convolutional layers may be passed to one or more un-pooling layers and/or one or more transposed convolutional layers. Through these layers, the extracted features may be up-sampled and further processed (e.g., via a plurality of deconvolution operations) to derive one or more up-scaled or dense feature maps or feature vectors. The dense feature maps or vectors may then be used to generate a reconstructed or denoised MRI image (e.g., image 106 of FIG. 1 or image 212 of FIG. 2).

Figure 3:
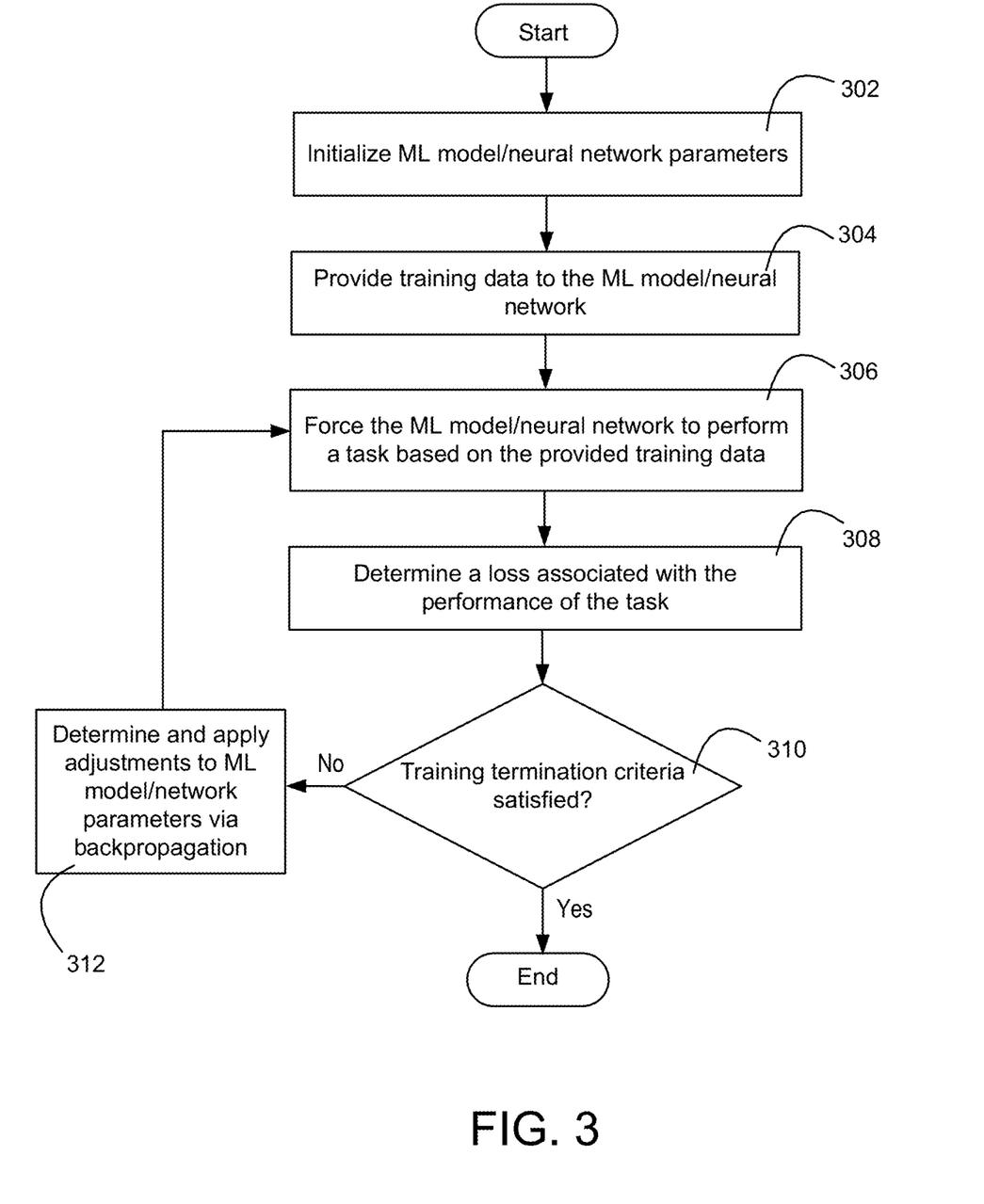
FIG. 3 is a flow diagram illustrating example operations that may be associated with the training of an ML model in accordance with one or more embodiments described herein.

FIG. 3 illustrates example operations that may be associated with training an ML model (e.g., an ANN used to implement the ML model) described herein. As shown, the training operations may include initializing parameters of the ML model or neural network (e.g., weights associated with the various filters or kernels of the neural network) at 302. The parameters may be initialized, for example, based on samples collected from one or more probability distributions or parameter values of another ML model or neural network having a similar architecture. The training operations may further include providing training data (e.g., an under-sampled MRI image or under-sampled MRI data) to the ML model or neural network at 304, and causing a task (e.g., predicting a reconstructed MRI image) to be performed using the ML model or neural network at 306 based on the provided training data.

At 308, a loss associated with the performance of the task (e.g., a reconstruction loss) may be determined, for example, by comparing the results (e.g., a reconstructed image) produced by the ML model or neural network with a ground truth (e.g., a fully-sampled MRI image). The loss may be determined using a suitable loss function such as a loss function based on a mean squared error (MSE), a structural similarity index measure (SSIM), an L1-norm, a peak signal-to-noise ratio (PSNR), etc. And once determined, the loss may be evaluated at 310 to determine whether one or more training termination criteria have been satisfied. For example, a training termination criterion may be deemed satisfied if the loss described above is below a predetermined thresholds, if a change in the loss between two training iterations (e.g., between consecutive training iterations) falls below a predetermined threshold, etc. If the determination at 310 is that a training termination criterion has been satisfied, the training may end. Otherwise, the loss may be backpropagated (e.g., based on a gradient descent associated with the loss) through the neural network at 312 before the training returns to 306.

For simplicity of explanation, the training steps are depicted and described herein with a specific order. It should be appreciated, however, that the training operations may occur in various orders, concurrently, and/or with other operations not presented or described herein. Furthermore, it should be noted that not all operations that may be included in the training process are depicted and described herein, and not all illustrated operations are required to be performed.

As described herein, MRI data (e.g., collected from a k-space) provided to an ML model (e.g., ML model 102 of FIG. 1 or ML model 210 of FIG. 2) in practical use cases may be inherently complex-valued. Thus, the training of the ML model should ideally also be conducted using complex-valued data to mimic the real world situations (e.g., such as phase sensitive image processing tasks). In reality, however, MRI images that may be used for model training are often stored in real-valued formats, such as Digital Imaging and Communications in Medicine (DICOM) formats, in which only the magnitudes of complex-valued MRI data (e.g., MRI images) may be retained. In addition, while modern MRI scanning technology may utilize multiple coils to simultaneously collect data from each coil, a finally saved DICOM image may be coil-combined and resemble only a single-coil image. Accordingly, an ML model trained using these real-valued, single-coil data may not be able to handle the complexity and diversity associated with real-world, complex-valued data. To improve the accuracy and adaptability of the ML model, complex-valued, multi-coil training data may be synthetically generated (e.g., using computer simulation), for example, based on real-valued, single-coil data and used for training the ML models described herein. When actual complexed-valued training data (e.g., collected from clinical procedures) are available, the synthetically generated MRI data may also be used together with the actual MRI data to train the ML models (e.g., the ML models may be trained using a mixture of actual and synthetically generated MRI data).

In examples, complex-valued MRI training data (e.g., MRI images) may be synthetically generated by adding phase information (e.g., artificial phase information) to real-valued MRI data or images. For instance, a first complex-valued MRI training dataset may be generated by adding respective first phase values to first real-valued MRI data (e.g., at one or more first spatial locations associated with the first real-valued MRI data) and a second complex-valued MRI training dataset may be generated by adding respective second phase values to second real-valued MRI data (e.g., at one or more second spatial locations associated with the second real-valued MRI data). To illustrate, a real-valued MRI image may be represented as $m(x, y, z)=|M(x, y, z)|$. By adding a phase $\theta(x, y, z)$ at each spatial location $(x, y, z)$, the real-valued image may be converted to a complex-valued image based on the following:

$$m(x, y, z)=|M(x, y, z)|*\exp(j\theta(x, y, z))$$

where j may represent an imaginary unit of a complex-valued number.

The spatial distribution of phase $\theta(x, y, z)$ may be parameterized or non-parameterized. In a parameterized example, the phase value at spatial location $(x, y, z)$ may be determined as a function (e.g., a first order linear function) of the spatial location such as the following:

$$\theta(x, y, z)=ax+by+cz$$

where a, b and c may be determined by fitting the function to existing phase data. In a non-parameterized example, the phase value at location $(x, y, z)$ may be determined (e.g., extracted) from one or more existing complex-valued images and applied to the real-valued (e.g., magnitude only) images. For instance, multiple existing complex-valued images may be averaged and the phase values of the averaged images may be added to the real-valued images. In examples, phase values may also be synthesized based on image $m(x, y, z)$. The synthesis may be performed using conventional methods like smoothing or using a deep learning based method in which a neural network may be trained to generate feasible phases based on real-valued (e.g., magnitude only) images.

Multi-coil MRI data (e.g., multi-coil MRI images) may be generated (e.g., synthesized) based on single-coil MRI data (e.g., single-coil MRI images). For example, multi-coil MRI images (e.g., for n coils) may be synthetically generated based on a single-coil MRI image and a set of coil sensitivity maps (e.g., simulated or synthesized coil sensitivity maps). Let $m(x, y, z)$ represent imagery data at location $(x, y, z)$ and let $C(x, y, z, p)$ represent a coil sensitivity map for a p-th coil, MRI data for the p-th coil at location $(x, y, z)$ may be calculated based on the following:

$$m(x, y, z, p)=C(x, y, z, p)*|M(x, y, z)|*\exp(j\theta(x,y,z))$$

where j, $|M(x, y, z)|$, and $\exp(je(x,y,z))$ may represent values described above. Accordingly, by simulating a first set of coil sensitivity maps associated with a first plurality of coils, a first multi-coil dataset may be generated based on a set of single-coil data, and by simulating a second set of coil sensitivity maps associated with a second plurality of coils, a second multi-coil dataset may be generated based on the set of single-coil data.

In examples, the coil sensitivity maps may be synthesized (e.g., simulated) using a spatial distributed function that may be parameterized. For instance, a coil sensitivity map for a p-th coil may be determined based on $C(x, y, z, p)=1/r((x, y, z),(xp, yp, zp))$, where $r(\ )$ may be a function used to calculate a distance between location $(x, y, z)$ and a center location $(xp, yp, zp)$ of the p-th coil (e.g., $r((x,y,z), (xp,yp,zp))=\sqrt{(x-xp)^2+(y-yp)^2+(z-zp)^2}$). In examples, the coil sensitivity maps may be extracted from an existing multi-coil image and processed before being applied to a single coil image. For example, multiple coil sensitivity maps may be calculated based on existing multi-channel MRI data before the multiple coil sensitivity maps are averaged or smoothed (e.g., based on polynomial fitting, by applying a filter, etc.).

Figure 4:
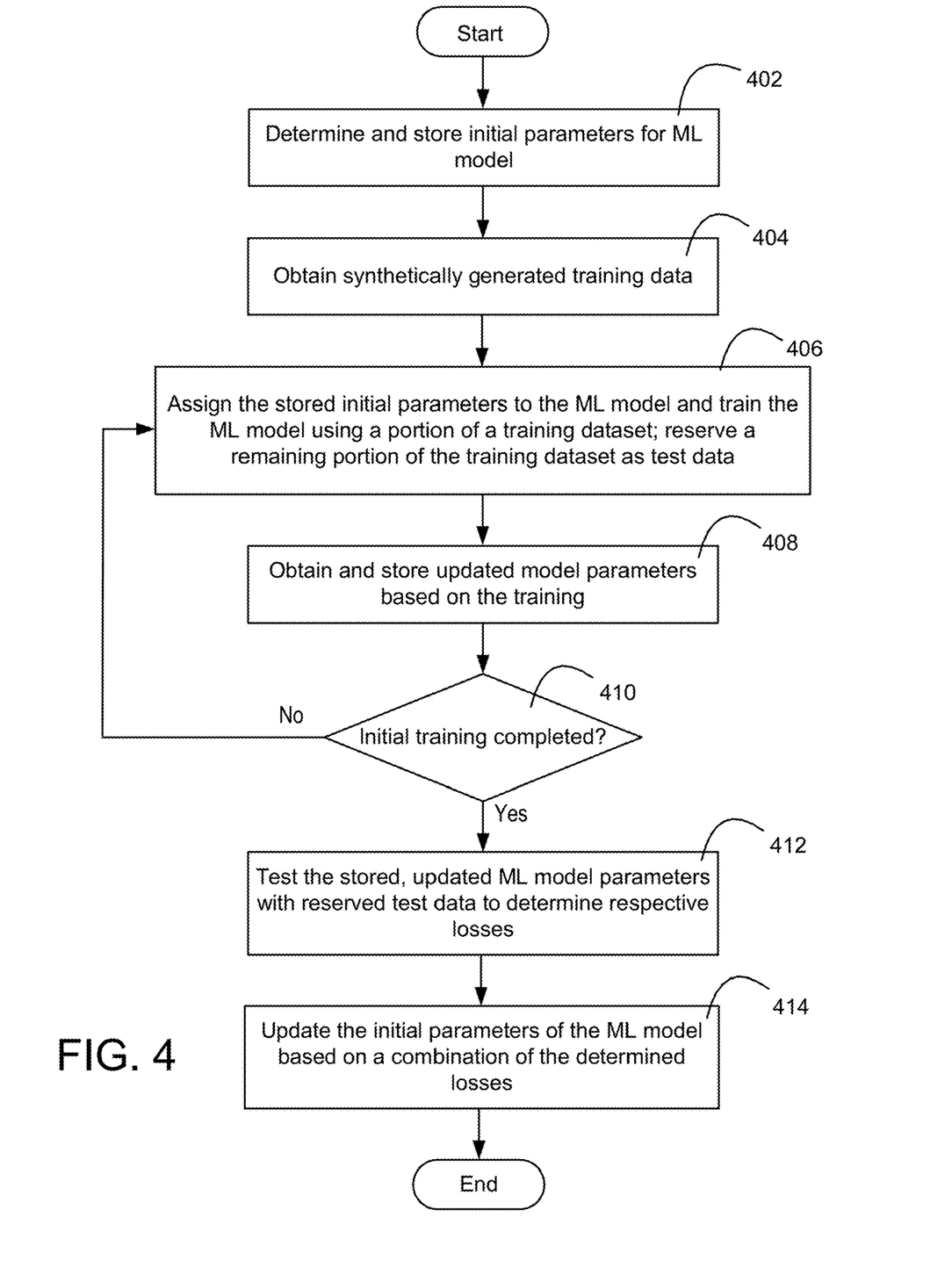
FIG. 4 is a flow diagram illustrating an example of a meta-learning process in accordance with one or more embodiments described herein.

The synthetically generated complex-valued MRI data may allow an ML model or an artificial neural network (e.g., such as the MRI image reconstruction neural network described herein) to be trained using realistic data such that the model or network may be able to handle practical MRI processing tasks at an inference time (e.g., when the model or network is deployed). To further enhance the adaptability of the ML model or neural network (e.g., to different data types), meta-learning based techniques may be adopted during the training of the ML model or neural network, as illustrated by FIG. 4. It should be noted that the illustrated meta-learning techniques may be applied to the training of ML models or neural networks for various tasks including MRI image reconstruction, image denoising, contrast enhancement, etc. It should also be noted that the illustrated meta-learning techniques may be applied in combination with (e.g., to supplement) the training of an ML model or neural network for a specific task such as the training process shown in FIG. 3.

As shown in FIG. 4, during the training of an ML model (e.g., a neural network used to implement the ML model), initial parameters, $P_{init}$, of the ML model (e.g., weights of the neural network) may be determined and stored at 402. The initial parameters may be determined, for example, based on one or more probability distributions or based on parameter values of another ML model or neural network having a similar architecture. At 404, training data to facilitate the meta-learning may be obtained. The training data may include actual complex-valued, multi-coil MRI images (e.g., or k-space data) that may be obtained from clinical practices and/or synthetic data may be generated, for example, using the data synthesis techniques described herein. For instance, let φ represent the parameters used in the data synthesis process described above (e.g., φ may include the values of a, b, c, r( ), (xp, yp, zp), etc., in the equations or formulas provided herein), by varying the values of φ, one or more sets of complex-valued, multi-coil MRI images or k-space data {y0, y1, . . . } may be synthetically generated based on parameters {φ0, φ1, . . . } and real-valued, single-coil MRI images or k-space data {x0, x1, . . . }, respectively.

At 406, stored initial parameters $P_{init}$ may be assigned to the ML model and a round of training may be conducted using the initial parameters and a portion of a first training dataset y0 (e.g., which may be synthetically generated using φ0 and x0 as described above). For example, training dataset y0 may include multiple complex-valued MRI images and a first portion y0_training of the MRI images may be used to conduct the training while a remaining portion y0_test of the MRI images may be reserved as test data for use during a later stage of the meta-learning. As a result of the training conducted using y0_training, a set of updated model parameters $P_{update0}$ may be obtained at 408, for example, by backpropagating a loss (e.g., via a single gradient descent step or a plurality of gradient descent steps) through the ML model (e.g., through layers of the neural network), and the updated model parameters may be stored for use during a later stage of the meta-learning.

At 410, a determination may be made regarding whether an initial stage of the meta-learning has been completed. The determination may be made, for example, based on the number of training datasets generated (e.g., y0, y1, y2 . . . ). If there are more training datasets left, the process described above may be repeated for each of the remaining training datasets. For example, with training datasets y1 (e.g., which may be synthetically generated using φ1 and x1 as described above), the stored initial parameters of the ML model, $P_{init}$, may be re-assigned to the ML model and another round of training may be conducted using the initial parameters and a portion of training dataset y1. Training dataset y1 may include multiple complex-valued MRI images and a first portion y1_training of the MRI images may be used to conduct the training while a remaining portion y1_test of the MRI images may be reserved as test data for use during a later stage of the meta-learning. As a result of the training conducted using y1_training, a set of updated model parameters $P_{update1}$ may be obtained, for example, by backpropagating a loss through the ML model (e.g., through layers of the neural network), and the updated model parameters may be stored for use during a later stage of the meta-learning.

For ease of description, only two training datasets (e.g., y0 and y1) are mentioned above. Those skilled in the art will appreciate, however, the meta-learning may be performed using more than two training datasets (e.g., including a third synthetically generated training dataset) and the operations described above may be repeated for the additional training datasets (e.g., including updating the ML model parameters based on the additional training datasets). Those skilled in the art will also appreciate that actual complex-valued MRI data may be used, for example, in addition to or in lieu of the synthetic data described herein, during the meta-learning process.

Referring back to FIG. 4, if the determination at 410 is that the initial stage of the meta-learning has been completed (e.g., all of the training datasets have been processed), the learning may proceed to 412 where the stored, updated ML model parameters (e.g., $P_{update0}$, $P_{update1}$, etc.) may be tested with the training data reserved for testing (e.g., y0_test, y1_test, etc.). For example, the testing may be performed by assigning updated model parameters (e.g., $P_{update0}$, $P_{update1}$, etc.) to the ML model and using those parameters to process the test data (e.g., y0_test, y1_test, etc.). As a result of the testing, respective losses associated with processing the test data with the updated model parameters may be determined, for example, based on a suitable loss function (e.g., MSE, SSIM, etc.) and ground truth associated with the processing task (e.g., the ground truth may be a fully-sampled MRI image for MRI image reconstruction). The determined losses (e.g., a combination of the losses) may then be used at 414 to update initial parameters $P_{init}$ of the ML model to obtain final (e.g., refined) parameters $P_{final}$ of the ML model. The update at 414 may be performed, for example, by backpropagating a sum or an average of the losses resulted from the testing (e.g., using test data y0_test, y1_test, etc.) through the artificial neural network.

Figure 5:
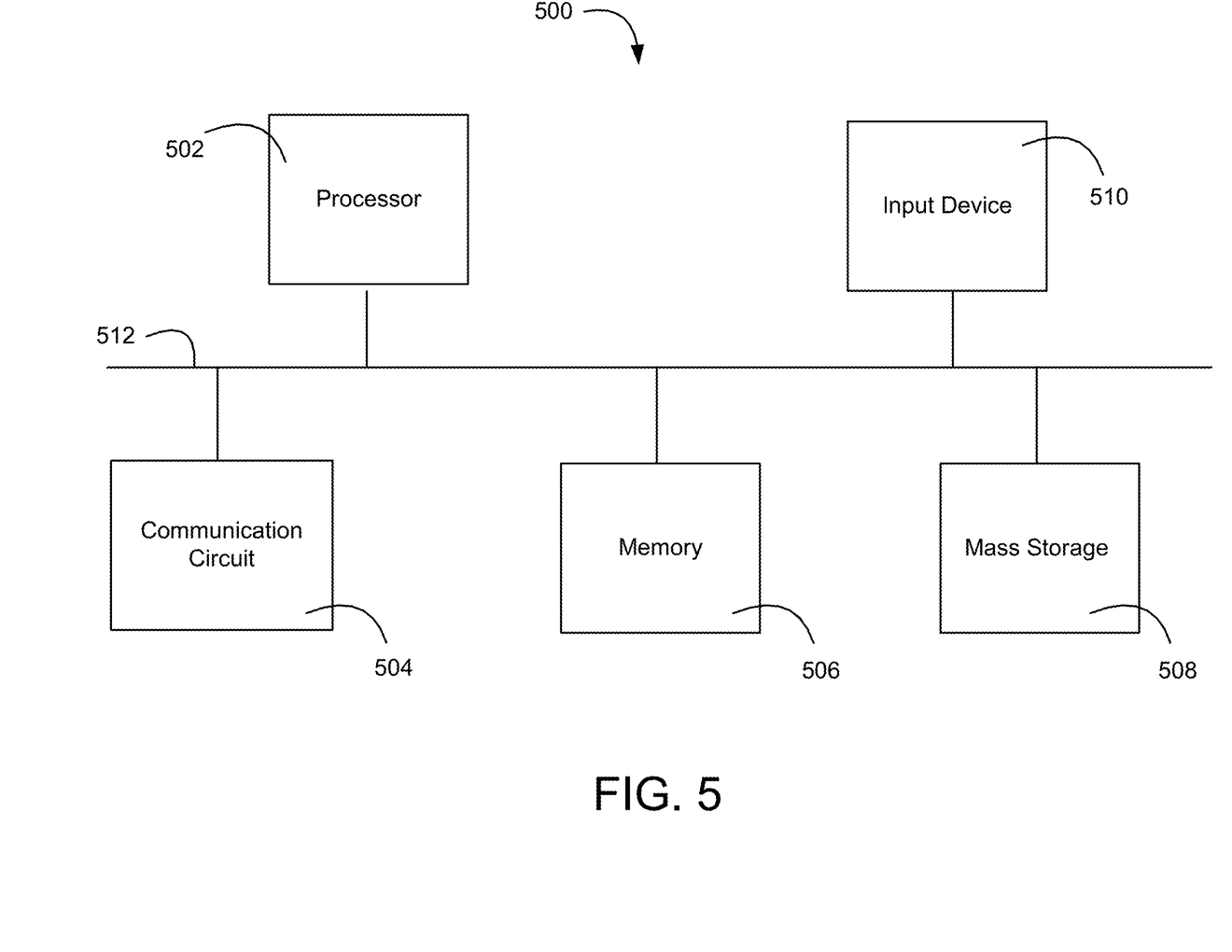
FIG. 5 is a simplified block diagram illustrating example components of an apparatus that may be configured to perform the tasks described in according with one or more embodiments provided herein.

The systems, methods, and/or instrumentalities described herein may be implemented using one or more processors, one or more storage devices, and/or other suitable accessory devices such as display devices, communication devices, input/output devices, etc. FIG. 5 is a block diagram illustrating an example apparatus 500 that may be configured to perform the MRI data processing tasks described herein. As shown, apparatus 500 may include a processor (e.g., one or more processors) 502, which may be a central processing unit (CPU), a graphics processing unit (GPU), a microcontroller, a reduced instruction set computer (RISC) processor, application specific integrated circuits (ASICs), an application-specific instruction-set processor (ASIP), a physics processing unit (PPU), a digital signal processor (DSP), a field programmable gate array (FPGA), or any other circuit or processor capable of executing the functions described herein. Apparatus 500 may further include a communication circuit 504, a memory 506, a mass storage device 508, an input device 510, and/or a communication link 512 (e.g., a communication bus) over which the one or more components shown in the figure may exchange information.

Communication circuit 504 may be configured to transmit and receive information utilizing one or more communication protocols (e.g., TCP/IP) and one or more communication networks including a local area network (LAN), a wide area network (WAN), the Internet, a wireless data network (e.g., a Wi-Fi, 3G, 4G/LTE, or 5G network). Memory 506 may include a storage medium (e.g., a non-transitory storage medium) configured to store machine-readable instructions that, when executed, cause processor 502 to perform one or more of the functions described herein. Examples of the machine-readable medium may include volatile or non-volatile memory including but not limited to semiconductor memory (e.g., electrically programmable read-only memory (EPROM), electrically erasable programmable read-only memory (EEPROM)), flash memory, and/or the like. Mass storage device 508 may include one or more magnetic disks such as one or more internal hard disks, one or more removable disks, one or more magneto-optical disks, one or more CD-ROM or DVD-ROM disks, etc., on which instructions and/or data may be stored to facilitate the operation of processor 502. Input device 510 may include a keyboard, a mouse, a voice-controlled input device, a touch sensitive input device (e.g., a touch screen), and/or the like for receiving user inputs to apparatus 500.

It should be noted that apparatus 500 may operate as a standalone device or may be connected (e.g., networked, or clustered) with other computation devices to perform the functions described herein. And even though only one instance of each component is shown in FIG. 5, a skilled person in the art will understand that apparatus 500 may include multiple instances of one or more of the components shown in the figure.

While this disclosure has been described in terms of certain embodiments and generally associated methods, alterations and permutations of the embodiments and methods will be apparent to those skilled in the art. Accordingly, the above description of example embodiments does not constrain this disclosure. Other changes, substitutions, and alterations are also possible without departing from the spirit and scope of this disclosure. In addition, unless specifically stated otherwise, discussions utilizing terms such as "analyzing," "determining," "enabling," "identifying," "modifying" or the like, refer to the actions and processes of a computer system, or similar electronic computing device, that manipulates and transforms data represented as physical (e.g., electronic) quantities within the computer system's registers and memories into other data represented as physical quantities within the computer system memories or other such information storage, transmission, or display devices.

It is to be understood that the above description is intended to be illustrative, and not restrictive. Many other implementations will be apparent to those of skill in the art upon reading and understanding the above description. The scope of the disclosure should, therefore, be determined with reference to the appended claims, along with the full scope of equivalents to which such claims are entitled.

What is claimed is:

1. An apparatus, comprising:
   one or more processors configured to:
   obtain magnetic resonance imaging (MRI) data; and
   process the MRI data using a machine learning (ML) model, wherein the ML model is learned through a training process that comprises:
   determining and storing initial parameters of the ML model;
   processing, based on the initial parameters of the ML model, a portion of a first MRI training dataset, wherein a first set of updated parameters of the ML model is determined as a result of processing the portion of the first MRI training dataset;
   processing, based on the initial parameters of the ML model, a portion of a second MRI training dataset, wherein a second set of updated parameters of the ML model is determined as a result of processing the portion of the second MRI training dataset;
   processing, based on the first set of updated parameters of the ML model, a remaining portion of the first MRI training dataset to determine a first loss;
   processing, based on the second set of updated parameters of the ML model, a remaining portion of the second MRI training dataset to determine a second loss; and
   updating the initial parameters of the ML model based on the first loss and the second loss.

2. The apparatus of claim 1, wherein at least one of the first MRI training dataset or the second MRI training dataset comprises complex-valued MRI data.

3. The apparatus of claim 2, wherein the complex-valued MRI data are synthetically generated based on real-valued MRI data and by adding phase values to the real-valued MRI data.

4. The apparatus of claim 3, wherein the phase values are derived from an MRI image or as a function of one or more spatial locations associated with the real-valued MRI data.

5. The apparatus of claim 1, wherein the at least one of the first MRI training dataset or the second MRI training dataset comprises multi-coil MRI data generated based on single-coil MRI data.

6. The apparatus of claim 5, wherein the multi-coil MRI data are generated by applying one or more coil sensitivity maps to the single-coil MRI data.

7. The apparatus of claim 6, wherein the one or more coil sensitivity maps are derived based on a spatial distribution function or a multi-coil MRI image.

8. The apparatus of claim 1, wherein the ML model is learned further by:
   processing, based on the initial parameters of the ML model, a portion of a third MRI training dataset, wherein a third set of updated parameters of the ML model is determined from the processing;
   processing, based on the third set of updated parameters of the ML model, a remaining portion of the third MRI training dataset to determine a third loss; and
   updating the initial parameters of the ML model further based on the third loss.

9. The apparatus of claim 1, wherein the initial parameters of the ML model are updated based on a sum or an average of the first loss and the second loss during the training process.

10. The apparatus of claim 1, wherein the MRI data comprises under-sampled MRI data and wherein the one or more processors being configured to process the MRI data comprises the one or more processors being configured to reconstruct an MRI image based on the under-sampled MRI data.

11. A method of processing magnetic resonance imaging (MRI) data, the method comprising:
   obtaining magnetic resonance imaging (MRI) data; and
   processing the MRI data using a machine learning (ML) model, wherein the ML model is learned through a training process that comprises:
   determining and storing initial parameters of the ML model;
   processing, based on the initial parameters of the ML model, a portion of a first MRI training dataset, wherein a first set of updated parameters of the ML model is determined as a result of processing the portion of the first MRI training dataset;
   processing, based on the initial parameters of the ML model, a portion of a second MRI training dataset, wherein a second set of updated parameters of the ML model is determined as a result of processing the portion of the second MRI training dataset;
   processing, based on the first set of updated parameters of the ML model, a remaining portion of the first MRI training dataset to determine a first loss;
   processing, based on the second set of updated parameters of the ML model, a remaining portion of the second MRI training dataset to determine a second loss; and
   updating the initial parameters of the ML model based on the first loss and the second loss.

12. The method of claim 11, wherein at least one of the first MRI training dataset or the second MRI training dataset comprises complex-valued MRI data.

13. The method of claim 12, wherein the complex-valued MRI data are synthetically generated based on real-valued MRI data and by adding phase values to the real-valued MRI data.

14. The method of claim 13, wherein the phase values are derived from an MRI image or as a function of one or more spatial locations associated with the real-valued MRI data.

15. The method of claim 11, wherein the at least one of the first MRI training dataset or the second MRI training dataset comprises multi-coil MRI data generated based on single-coil MRI data.

16. The method of claim 15, wherein the multi-coil MRI data are generated by applying one or more coil sensitivity maps to the single-coil MRI data.

17. The method of claim 16, wherein the one or more coil sensitivity maps are derived based on a spatial distribution function or a multi-coil MRI image.

18. The method of claim 11, wherein the ML model is learned further by:
   processing, based on the initial parameters of the ML model, a portion of a third MRI training dataset, wherein a third set of updated parameters of the ML model is determined from the processing;

processing, based on the third set of updated parameters of the ML model, a remaining portion of the third MRI training dataset to determine a third loss; and updating the initial parameters of the ML model further based on the third loss.

19. The method of claim 11, wherein the initial parameters of the ML model are updated based on a sum or an average of the first loss and the second loss during the training process.

20. The method of claim 11, wherein the MRI data comprises under-sampled MRI data and wherein processing the MRI data comprises reconstructing an MRI image based on the under-sampled MRI data.

* * * * *